US011567059B2

(12) United States Patent
Farchy et al.

(10) Patent No.: US 11,567,059 B2
(45) Date of Patent: Jan. 31, 2023

(54) PROFILER SYSTEM AND METHOD FOR MEASURING MULTIPHASE FLUID

(71) Applicant: AGAR Corporation, Inc., Houston, TX (US)

(72) Inventors: David Farchy, Bellaire, TX (US); Steven Bates, Sugar Land, TX (US); Efim Metsner, Cypress, TX (US); Hector Alfredo Viale-Rigo Capuzzo, Simonton, TX (US); Illenny Guevara, Katy, TX (US)

(73) Assignee: Agar Corporation, Inc., Houston, TX (US)

( * ) Notice: Subject to any disclaimer, the term of this patent is extended or adjusted under 35 U.S.C. 154(b) by 430 days.

(21) Appl. No.: 16/719,339

(22) Filed: Dec. 18, 2019

(65) Prior Publication Data
US 2020/0200728 A1 Jun. 25, 2020

Related U.S. Application Data

(60) Provisional application No. 62/782,219, filed on Dec. 19, 2018.

(51) Int. Cl.
*G01N 33/28* (2006.01)
(52) U.S. Cl.
CPC ................ *G01N 33/2823* (2013.01)
(58) Field of Classification Search
CPC .... G01N 33/28; G01N 33/2823; G01N 33/22; G01N 33/2835
See application file for complete search history.

(56) References Cited

U.S. PATENT DOCUMENTS

| 3,215,900 | A | * | 11/1965 | Oral | ................... G01N 33/2823 361/178 |
| 4,503,383 | A | | 3/1985 | Agar | |
| 4,519,415 | A | | 5/1985 | Carn | |

(Continued)

FOREIGN PATENT DOCUMENTS

| CN | 203396443 U | * | 1/2014 | |
| CN | 107796624 A | * | 3/2018 | ............ G01M 15/02 |

(Continued)

*Primary Examiner* — Tarun Sinha
*Assistant Examiner* — James I Burris
(74) *Attorney, Agent, or Firm* — Craft Chu PLLC; Andrew W. Chu

(57) ABSTRACT

The profiler system and method measure multiphase fluid with or without a container. The profiler includes at least one sensor module. Each sensor module extends a set distance from an upper end to a lower end of the module. This set distance determines proximal and distal measurement zones corresponding to different portions of multiphase fluid. The zones can be aligned within the container to define a sample volume with a relative position from top to bottom within the container. The profiler measures fluid characteristics with location data based on the sample volume or zones so that a profile of the multiphase fluid includes position of the portions of multiphase fluid measured. The safety and accuracy of storage in a container or active flow in a flow connector or open water can be maintained, even as the multiphase fluid dynamically changes while in storage and while in active flow.

18 Claims, 3 Drawing Sheets

(56) References Cited

U.S. PATENT DOCUMENTS

| | | | |
|---|---|---|---|
| 5,126,570 A * | 6/1992 | Boos | F02D 19/0628 |
| | | | 250/343 |
| 6,318,581 B1 | 11/2001 | Garton | |
| 2004/0206778 A1 | 10/2004 | Floyd et al. | |
| 2011/0214880 A1 | 9/2011 | Rogers | |
| 2011/0248801 A1* | 10/2011 | Blake | H01R 24/54 |
| | | | 333/24 R |
| 2013/0036588 A1 | 2/2013 | Agar | |
| 2017/0269053 A1* | 9/2017 | Ardrey | G01N 33/28 |

FOREIGN PATENT DOCUMENTS

| | | | |
|---|---|---|---|
| CN | 208239439 U * | 12/2018 | G01N 33/227 |
| DE | 29800967 U1 * | 4/1998 | G01N 1/2035 |

* cited by examiner

PROFILER SYSTEM AND METHOD FOR MEASURING MULTIPHASE FLUID

CROSS-REFERENCE TO RELATED APPLICATIONS

The present application claims priority under 35 U.S.C. Section 119(e) from U.S. Provisional Patent Application Ser. No. 62/782,219, filed on 19 Dec. 2018, entitled "SYSTEM AND METHOD FOR MEASURING MULTIPHASE FLUID IN A CONTAINER".

See also Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention relates generally to a profiler system and method for monitoring and multiphase composition measurements. In particular, the present invention relates to a profiler system and method to determine fluid characteristics in different portions of a dynamic multiphase fluid. More particularly, the present invention relates to identifying components of a multiphase fluid at different levels from top to bottom of a container.

2. Description of Related Art Including Information Disclosed Under 37 CFR 1.97 and 37 CFR 1.98

Fluids in the oil and gas industry often are multi-phase fluids that contain oil, gas, solids, chemical additives, gas, aqueous phases, and water. These fluids are stored in containers, and it is required to identify the contents in the container. Containers include a wide variety of vessels, ranging from manufactured tanks, such as storage tanks with very controlled inlets and outlets and set volume to natural formations, such as lakes, caves, and pools. The composition, flow rate, and viscosity of each component will vary. These fluids can also present in devices that are not containers, such as the multiphase fluids being transported between containers through flow connectors, like pipes, conduits, and channels, and multiphase fluids in open water, such as oceans. The multiphase fluids without containers flow and move.

There are concerns for storing and mixing the fluid in any container. Whether the container is filled, partially filled, or being emptied can affect the safety and efficiency of the dynamic multiphase fluid. There are concerns for flowing the fluid without a container. Whether a flow connector has turbulence or a sufficient pipe diameter can also affect the safety and efficiency of transporting the dynamic multiphase fluid between containers. Whether there is an oil leak in the ocean can affect the stability and safety of oil production at a subsea location.

Different phase components settle within the container, pass at different flow rates within a flow connector, and settle in open water, such that the contents are not uniformly distributed. Different components separate by density, and the same components stored in the container at different times may not be settled to the same level, depending upon the time. The same components passed through a pipe may have different flow rates and different settling in an active flow. Similarly, in open water, there is active flow of the different components of a multiphase fluid. The proper additives and reactions must be controlled and safe, and the controlled pumping of the fluid between containers must be safe in the container and in the flow connector. Natural flow of the fluid must also be safe in open water.

Testing the fluid in a container or a flow connector or open water can create a profile of the contents. The profile includes the components and conditions of the components. The profile is used to determine characteristics of the fluid and safety precautions. It is important for safety and production efficiency to identify portions of the fluid accurately. Within a container, the fluid characteristics, including phases, can be mapped on the three dimensions of the container. There are also multiphase fluids without containers, such as multiphase fluids in flow connectors and in open water. Situations, like oil spills or oil leaks, may need to be detected, when there is no actual container for the multiphase fluid. Without a container, the fluid characteristics, including phases, can be mapped on the three dimensions based on the profiler itself.

It is an object of the present invention to provide a system and method to identify components of a multiphase fluid in a container.

It is an object of the present invention to provide a system and method to determine a profile of the contents of a manufactured tank, natural formation, flow connector, or open water.

It is another object of the present invention to provide a profile of the contents relative to the location within a storage tank.

It is another object of the present invention to provide a profile of the contents to identify the individual phases of a multiphase fluid, including interfaces between phases and mixtures of different phases.

It is an object of the present invention to provide a profiler to measure portions of a multiphase fluid without a container.

It is another object of the present invention to provide a position profile of a sample supply of multiphase fluid with or without a container.

These and other objectives and advantages of the present invention will become apparent from a reading of the attached specification.

BRIEF SUMMARY OF THE INVENTION

Embodiments of the present invention include the system to measure multiphase fluid in a container with a profiler and the profiler itself with or without a container. A container, including a manufactured tank, a natural formation, and flow connector, stores multiphase fluid. A flow connector, including a pipe or conduit, also stores multiphase fluid, even if temporarily and even if for less time than a container. The multiphase fluid contains different fluids, such as oil, water, and other fluids. There are particles and other additives mixed within the fluid. With different densities and fluid speeds, the rheological properties or fluid properties of the multiphase fluid fluctuates. The fluid properties are not uniform through the fluid settling in the container or passing through the flow connector or settling in the ocean, and these fluid properties continue to fluctuate while stored in the container, while pumped through the flow connector, and while being present in the ocean, respectively. Once filled into the container or flow connector or open water, the multiphase fluid may continue to fluctuate with heavier fluids sinking and less dense fluids rising by gravity to the top of the container or top of a pipe or top ocean surface. There is a striation of levels from top to bottom by gravity, depending on gravity and other factors, such as turbulence. The multiphase fluids without a container, such as flow connectors and open water, also have flow rates of different phases. The fluid properties of the multiphase fluid vary at different locations within the container or flow connector or open water.

The present invention allows measurement of the multiphase fluid simultaneously at different locations within the manufactured tank or natural formation so that a profile of the fluid properties within the container can be determined and mapped. The profile, such as a position profile, allows for safer working conditions. The different types of fluids can be identified by physical location so that proper safety measures can be taken during filling, storing, and emptying a manufactured tank or natural formation and during pumping through a flow connector. Additionally, other fluid properties, such as flow rate and temperature can be maintained with safe conditions.

Embodiments of the present invention as a system includes a container being comprised of a container body with a top end and a bottom end below the top end. Containers may include any vessel to hold multiphase fluid, such as manufactured tanks, and natural formations. Some containers, such as storage tanks, can have an inlet on the top surface. The natural formation can be containers, such as lakes and caves. The natural formations can have irregular shapes and even dynamic shapes; however, there are still top ends and bottom ends of these natural formations relative to gravity. By gravity, the multiphase fluid would be at the bottom end and fill the container toward the top end. The present invention also includes a profiler being comprised of a sensor module, a flange connector, and a flange cap. The flange connector is oriented closer to the top end, while the flange cap is oriented closer to the bottom end so that the profiler remains suspended within the interior of the container. The sensor module has an upper end and a lower end opposite the upper end. There is a set distance from the upper end to the lower end. The profiler in the system can be inserted within the container from the top end, according to the set distance, and the set distance is aligned within the container. The lower end extended from the upper end of the sensor module is aligned with a set portion of the container body, particularly, from the top end toward the bottom end of the container. The set portion of the container body defines a sample volume of the container with a relative position from the top end to the bottom end within the container. The sensor module is aligned with the sample volume of the container so as to simultaneously measure fluids within the entire set portion of the container body.

Alternate embodiments of the present invention include the profiler itself. This embodiment of the sensor module has a proximal end and a distal end opposite the upper end, instead of an upper end and lower end. The profiler itself allows a position profile to be created in a flow connector or other open water without an actual container to hold the multiphase fluid. The profiler itself can be used in active flow situations that do not have containers. The multiphase fluid is not contained because the multiphase fluid actively flows. The set distance is now from a distal end to a proximal end (instead of lower end to upper end of in the container embodiment) so as to form a proximal measurement zone and a distal measurement zone. The proximal measurement zone corresponds to a proximal portion of a sample supply of multiphase fluid, and the distal measurement zone corresponds to a distal portion of the sample supply of multiphase fluid. The proximal measurement zone is separated from the distal measurement zone by the set distance so as to simultaneously measure fluids within the proximal measurement zone and the distal measurement zone according to relative position of the proximal portion and the distal portion.

Embodiments of the sensor module include a first sensor attached to the flange connector and extending toward the lower end, a first ground ring attached to the first ground electrode, and a second sensor extending toward the lower end from the first ground ring. Each sensor includes an antenna body extending from the flange connector to the lower end; and a ground electrode extending along the antenna body from the flange connector to the lower end. The sensor module is modular, so a second ground ring and a third sensor can be added. A third ground ring, and fourth sensor can also be added. The embodiments of the system further include a pipe connection flange attached to the top end of the container body and removably attached to the flange connector, a flexible joint connected to the pipe connection flange, a coaxial cable transition box attached to the flexible joint.

Another alternative embodiment is the method of measurement, including the step of installing a profiler in a sample supply of multiphase fluid, measuring fluid characteristics of the proximal portion of the sample supply at the proximal measurement zone, measuring fluid characteristics of the distal portion of the sample supply at the distal measurement zone simultaneous with the step of measuring fluid characteristics of the proximal portion; and determining a position profile of fluid characteristics of the sample supply of multiphase fluid based on the set distance of the sensor profile. The method includes installing the profiler in multiphase fluid with or without a container. The method with simultaneous measuring in different physical locations within the multiphase fluid provides a more complete and accurate profile of fluid characteristics.

DETAILED DESCRIPTION OF THE INVENTION

Multiphase fluid is comprised of different fluids, liquids, particles, gases, dissolved gases, and possibly other solids. For example, wellbore fluids in the oil and gas industry are often multiphase fluids that contain oil, gas and water. The composition, flow rate, and viscosity of each component (oil, water, and gas) vary from filling a container, storing in the container, and emptying the container. Containers include a wide variety of vessels. There are manufactured tanks, such as storage tanks with set inlets, outlets and interior volume. There are natural formations, such as lakes, caves, oceans, and pools, with irregular shapes and changing shapes.

Gases may be lighter and rise to the top of any of these containers, when stored in the container for a specific amount of time. Denser liquids and particles may settle towards the bottom, depending on the duration of time spent in the container. A large variety of flow patterns within the container, physical compositions, and fluid properties are distributed throughout the container. One sensor in the container is unable to simultaneously measure in more than one location. More than one sensor is also insufficient, since the multiphase fluid is dynamic and changing. There must be a particular relationship between multiple sensors in order for relevant measurements to be gathered. These multiphase fluids are stored in all types of containers, and it is required to identify the contents in the container. The composition, flow rate, and viscosity of each component will vary.

The composition, flow rate, and viscosity of each component (oil, water, and gas) of a multiphase fluid also vary in active flow without a container, such as pumping fluid between containers through a pipe or settling in open water. Flow connectors, like pipes, conduits, and channels, not containers for multiphase fluid because there is always active flow. For example, pipes may be horizontal or angled. In the active flow without a container, the top side of a horizontal pipe is not comparable to the top end of a container, since there is active flow and the effect of gravity is not the same. However, the present invention remains applicable to these sample supplies of multiphase fluid. The same particular relationship between multiple sensors in order for relevant measurements to be gathered can be applied in active flow without a container. These multiphase fluids in active flow can still be identified by contents, composition, flow rate, and viscosity of each component.

Figure 1:
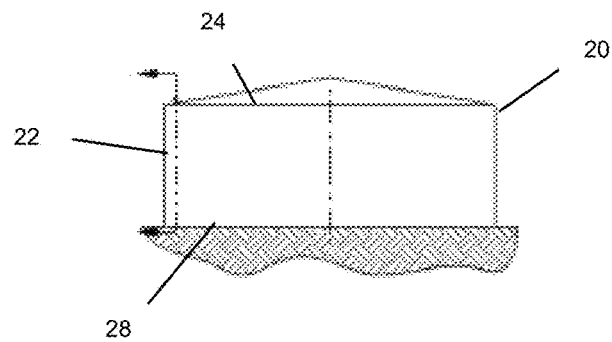
FIG. 1 is a schematic view of a container, according to an embodiment of the system of the present invention.
Figures 2, 3, 4:
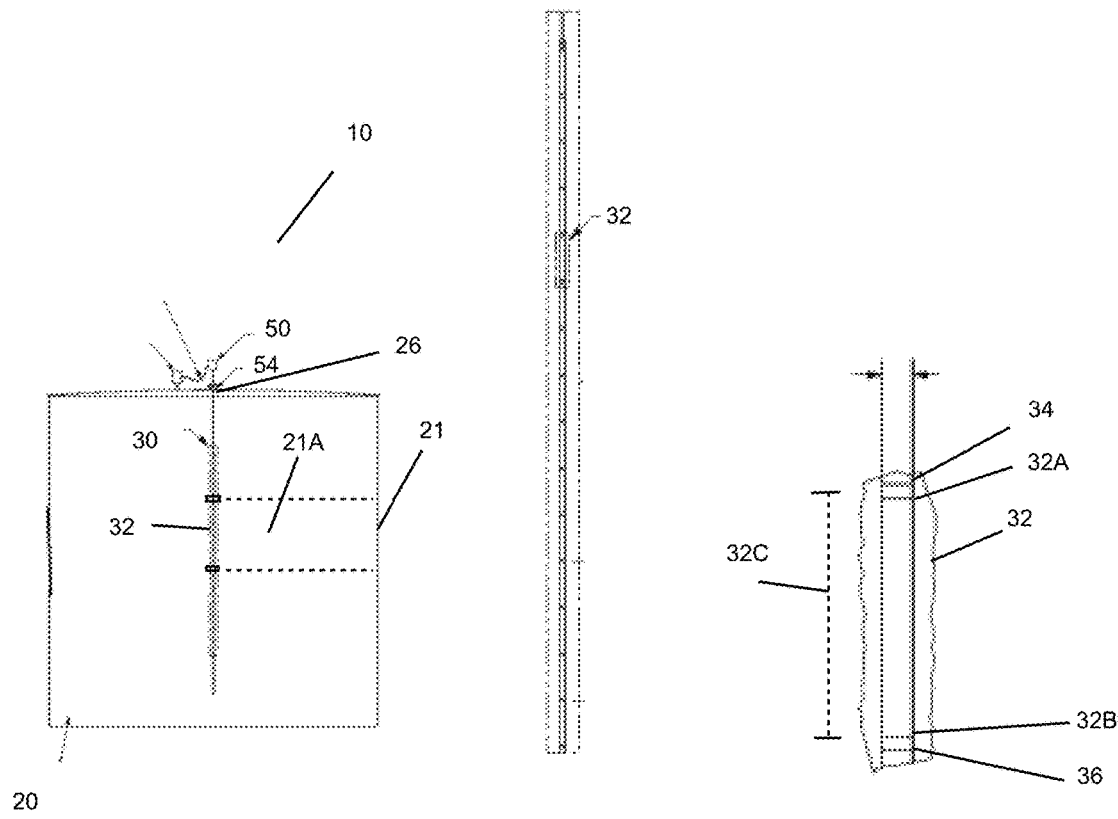
FIG. 2 is a schematic view of the system and method for measuring a multiphase fluid in a container, according to embodiments of the present invention.
FIG. 3 is an isolated schematic view of a profiler of the system, according to an embodiment of the present invention.
FIG. 4 is an isolated schematic view of a sensor module on the profiler of the system, according to an embodiment of the present invention.

Referring to FIGS. 1-8, the system 10 of the present invention measures a sample supply of multiphase fluid. In the embodiment of FIGS. 1-7, the system 10 includes a container 20 with a profiler 30. The container 20, such as a manufactured tank, natural formation or flow connector, stores multiphase fluid with different rheological properties or fluid properties throughout the container. FIGS. 1-2 show the container 20 being comprised of a container body 22 with a top end 24 and a bottom end 26 below the top end. FIG. 2 shows an embodiment with an inlet 26 on the top end. The inlet 26 is accessible from above the container 20. Other containers (not shown) include natural formations, like caves and lakes. The top end may have an open top, like a lake.

FIGS. 2-4 show embodiments of the profiler 30 in the system 10 being comprised of a sensor module 32 having an upper end 32A and a lower end 32B opposite the upper end, a flange connector 34 at the upper end, and a flange cap 36 at the lower end. FIG. 2 shows the system 10 with the profiler 30 extending into the container 20 through the inlet 26. The profiler 30 extends from the top end 24 to the bottom end 26. FIG. 4 shows the lower end 32B extending a set distance 32C from the upper end 32A. This set distance is aligned within the container 20. The lower end 32B extended from the upper end 32A is aligned to extend from the top end 24 toward the bottom end 26 of the container. The alignment of the profiler 30 relative to the container 20 defines a set portion 21 of the container body 22 between the top end 24 and the bottom end 26. The alignment includes the profiler 30 being parallel to the direction from the top end 32A to the bottom end 32B of the container 20, being orthogonal to the direction from the top end 32A to the bottom end 32B of the container 20, and any angle between parallel and orthogonal. The profiler 30 can be installed from any angle from the top end 32A or from any entry point even on a side of the container 20. The profiler 30 can even be floated in the container.

The relationship between the profiler 30 and the container body 22 defines a set portion 21 of the container 20 corresponding to a sample volume 21A of the container 20 with a relative position within the container 20. The sample volume 21A must define a three-dimensional sample supply of multiphase fluid. The system 10 measures this sample supply of multiphase fluid in the sample volume 21A. In particular, the profiler 30 simultaneously measures two different portions of the sample supply in a spatial relationship to each other that allows a position profile to be created. The sensor module 32 is aligned with the sample volume 21A of the container 20 so as to simultaneously measure more than one location of multiphase fluid in the container 20. With the relative position of the set portion 21 between the top end 24 and the bottom end 26 known, the fluid characteristics can be determined according to physical location so that a profile of the multiphase fluid at different levels within the container 20 can be determined. The profile is a position profile. The relative position from top end 24 to bottom end 26 is important so that fluid characteristics can be identified at different levels. When pumping out from the bottom end 26 of the container 20, the safety conditions of the multiphase fluid can be set according to the profile of multiphase fluid. For example, with lighter gases closer to the bottom end 26, the flow rate for pumping out of the container 20 may need to be adjusted for the lower viscosity. There could be lighter gases at the bottom end 26, if the multiphase fluid had not been stored in the container 20 long enough for the lighter gases to rise to the top end 24. The present invention now provides this important data for improved work conditions related to pumping and storing multiphase fluid.

Figure 8:
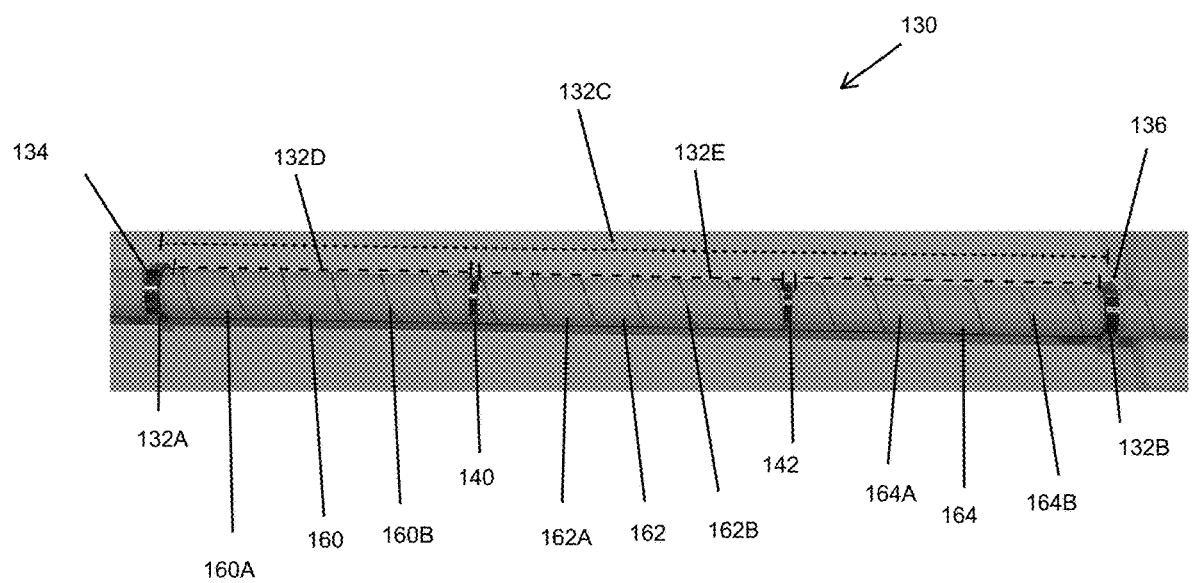
FIG. 8 is an elevation view of another embodiment of the present invention as a profiler itself.

FIGS. 3, 4 and 8 show the embodiment of the present invention as the profiler 130 itself. The profiler 130 can be positioned within a sample supply of multiphase fluid in active flow without a container. There can be a profiler 130 in a flow connector, like a pipe in FIG. 8 with the proximal end 132A instead of a top end of a container. Flow connectors, like a channel (not shown) could also have an open top. Additionally, the multiphase fluid in active flow includes open water, such as the ocean. The profiler 130 can be floated by a balloon or buoy into the multiphase fluid, such as an oil spill or oil leak detection situation.

The sensor module 132 has a proximal end 132A and a distal end 132B opposite the upper end. There is a proximal end 132A and distal end 132B instead of an upper end 32A and a lower end 32B. The profiler 130 also includes a flange connector 134 at the proximal end, and a flange cap 136 at the distal end. The distal end extends a set distance 132C from the proximal end so as to form a proximal measurement zone 132D and a distal measurement zone 132E. These zones are comprised of parts of exterior surfaces of the sensor module 132 and the volume immediately around these parts of exterior surfaces. The portions of multiphase fluid of the sample supply in the volume immediately around the exterior surfaces can be measured to determine the profile of the overall sample supply. The proximal measurement zone corresponds to a proximal portion of the sample supply of multiphase fluid, and the distal measurement zone corresponds to a distal portion of the sample supply of multiphase fluid. The proximal portion is different from the distal portion by spatial position. In particular, the proximal measurement zone is separated from the distal measurement zone by the set distance so as to simultaneously measure fluids within the proximal measurement zone and the distal measurement zone according to relative position of the proximal portion and the distal portion.

The other embodiments of the profiler 130 of FIGS. 3, 4 and 8 include incorporating a container comprised of a container body with a top end and a bottom end below the top end. In those embodiments, the proximal end 32A is oriented closer to the top end, and the distal end 32B is oriented closer to the bottom end. The profiler 130 is not necessarily vertical; however, there is a three dimensional relationship between the proximal measurement zone 132D and the distal measurement zone 132E for the profiler 130 to create a profile based on the position of the proximal measurement zone and the distal measurement zone.

In both embodiments of the system 10 and the profiler 130 itself, the sensor module 32, 132 can be comprised a first sensor 60, 160 attached to the flange connector 34, 134 and extending toward the lower end 32B/distal end 132B, a first ground ring 40, 140, and a second sensor 62, 162 extending toward the lower end 32B/distal end 132B from the first ground ring 40. The first sensor 60, 160 is comprised of a first antenna body 60A, 160A extending from the flange connector 34, 134 to the lower end 32A/distal end 132A, and a first ground electrode 60B, 160B extending along the first antenna body 60A, 160A from the flange connector 34, 134 to the lower end 32A/distal end 132A. Similarly, the second sensor 162 is comprised of: a second antenna body 62A, 162A extending from the first ground ring 40, 140 to the lower end 32A/distal end 132A, and a second ground electrode 162B extending along the second antenna body 62A, 162A toward the lower end 32A/distal end 132A. The first ground ring 40/140 can be attached to the first ground electrode 60A, 160A. The first ground electrode 60B, 160B and the second ground electrode 62B, 162B can each be spiral ground electrodes coiled or wrapped around the respective antenna bodies 60A, 160A, 62A, 162A. Other shapes of ground electrodes are possible, although all ground electrodes 60B, 160B, 62B, 162B of the present invention must span a respective set distance 32C, 132C of the profiler 30, 130. In the embodiment of the system 10 of FIGS. 1-2, the first antenna body 60A and the second antenna body 62A extend through the set portion 21 of the container body 22. In the embodiment of the profiler 130 of FIG. 8, the first antenna body 160A and the second antenna body 162A extend through the proximal measurement zone 132D and the distal measurement zone 132E.

In both embodiments of the system 10 and the profiler 130 itself, the sensor module 32, 132 is modular. Each sensor module 32, 132 can further include a second ground ring 42, 142, and a third sensor 64, 164 extending toward the lower end 32B/distal end 132B from the second ground ring 42. The third sensor 64, 164 is comprised of a third antenna body 64A, 164A extending from the second ground ring 42, 142 to the lower end 32A/distal end 132A, and a third ground electrode 64B, 164B extending along the third antenna body 64A, 164A from the second ground ring 42, 142 to the lower end 32A/distal end 132A. The second ground ring 42/142 can be attached to the second ground electrode 62A, 162A. In the embodiment of the system 10 of FIGS. 1-2, the first antenna body 60A, the second antenna body 62A, and the third antenna body 64A extend through the set portion 21 of the container body 22. In the embodiment of the profiler 130 of FIGS. 7-8, the first antenna body 160A, the second antenna body 162A, and the third antenna body 164A extend through the proximal measurement zone 132D and the distal measurement zone 132E. As a modular component, each sensor module 32, 132 can also include a third ground ring (not shown) and a fourth sensor (not shown) in an analogous relationship to the other ground rings 40, 42, 140, 142 and other sensors 60, 160, 62, 162, 64, 164.

Figure 5:
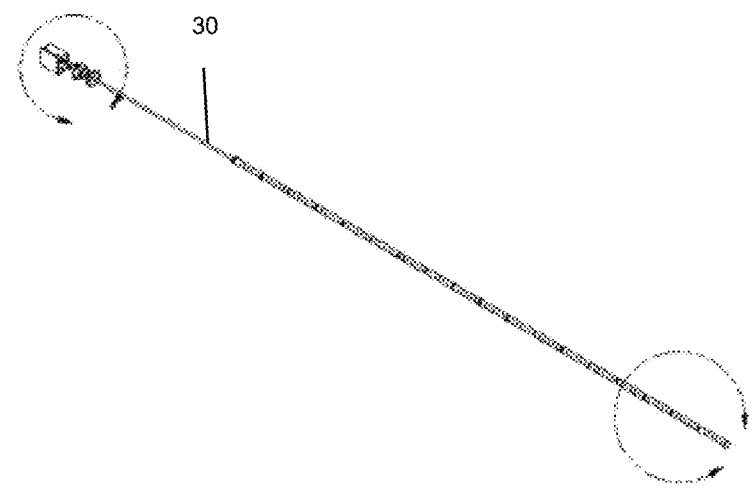
FIG. 5 is a perspective view of the profiler of the system, showing additional components of the system for attachment to the container, according to embodiments of the present invention.
Figure 6:
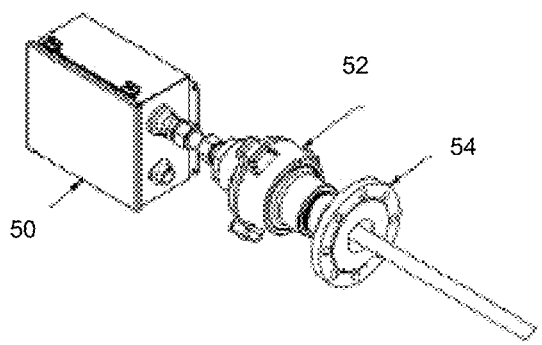
FIG. 6 is an isolated schematic view of a coaxial cable transition box, flexible joint, and pipe connection flange for the profiler in FIG. 5.
Figure 7:
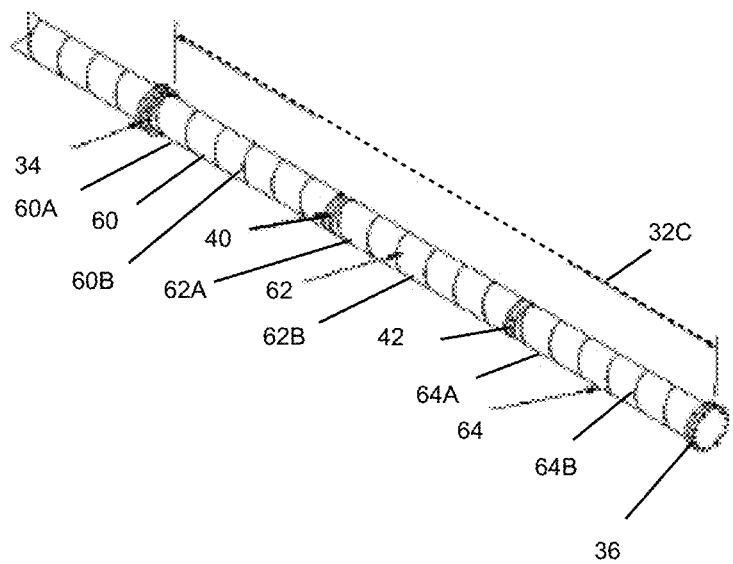
FIG. 7 is an isolated schematic view of the profiler of the present invention.

FIGS. 2, 5, and 6 show the system 10 comprising a pipe connection flange 54 attached to the top end 24 of the container body 22 and removably attached to the flange connector 34, a flexible joint 52 connected to the pipe connection flange 54, and a coaxial cable transition box 50 attached to the flexible joint 52. The flexible joint 52 allows the profiler 30 to swivel within the container 20, as seen in FIG. 2. With active fluid flow, the profiler 30 must have some flexibility to adjust in order to prevent damage. The coaxial cable transition box 50 allows electrical connections to the profiler 30 from outside the container 20. Data and power can be transmitted to and from the profiler 30 even from the lower end 36 for reliable communication of the fluid properties being measured. Similarly, in the embodiment of the profiler 130 itself in FIG. 8 with a container, that container may also include a pipe connection flange, a flexible joint, and a coaxial cable transition box.

Embodiments of the present invention include the method of measurement for multiphase fluid. The method includes the step of installing a profiler 30, 130 in a sample supply of multiphase fluid. The sample supply can be in a container 20 for a profiler 30 of FIGS. 1-2 or in active flow, as shown in FIG. 8 for profiler 130. The method includes measuring fluid characteristics of the proximal portion of the sample supply at the proximal measurement zone 132D and measuring fluid characteristics of the distal portion of the sample supply at the distal measurement zone 132E simultaneous with the step of measuring fluid characteristics of the proximal portion. The method further includes determining a position profile of fluid characteristics of the sample supply of multiphase fluid based on the set distance 32C, 132C of the sensor module 32, 132. profile.

In the embodiment of the method with a container 20, the container 20 is comprised of a container body 22 with a top end 24 and a bottom end 26 below the top end, wherein the upper end 32A/proximal end 132A is oriented closer to the top end, and the lower end 32B/distal end 132B is oriented closer to the bottom end. The container body 22 has a set portion 21 between the top end and the bottom end. The set portion is now aligned with the set distance so as to define a sample volume 21A of the container with a relative position within the container. The sample volume of the container corresponds to the proximal portion of the sample supply and the distal portion of the sample supply. The position profile of fluid characteristics of the sample supply of multiphase fluid corresponds to the sample volume of the container. The fluid characteristics and the physical location of these fluid characteristics within the sample supply of multiphase fluid are measured and mapped based on the set distance of the profiler 30, 130. The set distance 32C for a container embodiment is mapped to a physical location within the container 20. The set distance 132C with or without a container is mapped to a physical location of the portions of multiphase fluid, which can be tracked from flow rates measured in the proximal measurement zone and distal measurement zone of the profiler 130.

Unlike other probes and sensors, the embodiments of the system 10 and the profiler 130 itself of the present invention identify components of a multiphase fluid. The fluid characteristics are measured, and the physical location of these components are mapped. In the system 10 with a container, there is no movement of the profiler 30 between the top end 24 and the bottom end 26. Prior art ball sensors float through the multiphase fluid and cause fluid flow and turbulence within the container. These fluctuations are no longer caused by the profiler 30 of the present invention. Vertical movement of the sensor no longer impacts the accuracy of measurements of fluid properties in creating the profile of the container 20.

Embodiments of the present invention can create a profile of the multiphase fluid, in particular, a position profile. The multiphase fluid can be mapped in a container, such as a manufactured tank or underground cave, according to locations at different levels relative to a top end and bottom end of the various containers. The contents have different composition, flow rate, and viscosity. There are fluctuations in the material composition, mixture, density, temperature, viscosity, and flow rate as the multiphase fluid is delivered into the container, stored in the container, and released from the container. A single probe will only measure one location or at least only one point between the top and bottom of the container. This isolated measurement does not allow the contents to be fully understood.

When the single probe is moved, such as raised and lowered within the container, the single probe can take measurements for more than one location. These additional measurements can create a better estimation of the contents of the container than the measurement at a single location. However, the movement of the single probe itself causes turbulence and disturbs the settling of the multiphase fluid. The present invention addresses this "observer effect" from particle physics in the field of multiphase fluid measurement. The system with the profiler of the present invention identify components of a multiphase fluid and determines a profile of the contents of a container as a manufactured tank, natural formation, or flow connector. The alignment of the set distance of the sensor module relative to the set portion of the container body defines a sample volume with a relative position between the top end and bottom end of the container body. The measurements of the multiphase fluid in the sample volume are now associated with the set portion of the sensor module and the set distance of the sensor module. This relationship of the sensor module and container body allow the mapping of the measurements at locations at different levels between the top end and the bottom end. The system of the present invention measures a cross-section of the multiphase fluid in the container, instead of a single point. With these relative positions of the measurements, a profile can be created to map the contents of the multiphase fluid from top to bottom of the container.

In some embodiments, the measurements can continuously to create an active profile of the multiphase fluid, accounting for fluid flow within the container. As the multiphase fluid fluctuates, the system of the present invention measures the fluctuates to allow for tracking. The rise of a lighter gas fluid can be tracked in real time, so that safety precautions can be taken to account for gas accumulating at the top end of the container. Additionally, the interfaces between different phases and mixtures of different phases can be measured relative to the top and bottom of the container. The present invention now provides this important data for improved work conditions related to pumping and storing multiphase fluid.

Additionally, the present invention is only attached at the top end of the container. The profiler can swivel for some flexibility to withstand fluid movement without damage. There is no anchor at the bottom end so that the installation of the system is easier and more efficient. The profiler can be inserted before, during, or after, without having to align with an anchor on the bottom end. The alignment of the profiler includes the profiler being parallel, orthogonal, or any angle between parallel and orthogonal. The profiler can be installed from any angle from the top end or from any entry point even on a side of the container. The profiler can even be floated in the container. With the set distance being known, the profile can be a position profile to identify the composition in the container as settling happens in real time. The modular feature allows adjustable dimensions for different containers, and the single inlet at the top end allows for real time adjustments during installation.

Even without a container, the embodiments of the profiler itself can determine a position profile of the multiphase fluid. The proximal measurement zone and the distal measurement zone of the profile itself provide location data for the corresponding portions of sample supply of multiphase fluid measured at each zone. This relationship to the profiler still provides location data that can form a position profile, even without the confines of any of the containers of the present invention. For example, flow rate of the portion measured at the proximal measurement zone and distal measurement zone can determine a physical location of that portion further down the pipe. The present invention allows a profile of multiphase fluid in active flow in a flow connector or open water, in addition to a profile in a container.

The foregoing disclosure and description of the invention is illustrative and explanatory thereof. Various changes in the details of the illustrated structures, construction and method can be made without departing from the true spirit of the invention.

We claim:
1. A system for measuring multiphase fluid, comprising:
a container being comprised of a container body with a top end and a bottom end below said top end; and
a profiler being comprised of:
a sensor module having an upper end and a lower end opposite said upper end, said lower end extending a set distance from said upper end;

a flange connector at said upper end; and
a flange cap at said lower end,
wherein said set distance is aligned within said container, said lower end extended from said upper end and from said top end toward said bottom end,
wherein said container body has a set portion between said top end and said bottom end, said set portion being aligned with said set distance so as to define a sample volume of said container with a relative position within said container,
wherein said sensor module is aligned with said sample volume of said container so as to span said sample volume with said sensor module and simultaneously measure fluids within said set portion of said container according to relative position of said set distance within said container, and
wherein said sensor module is comprised of:
a first sensor attached to said flange connector and extending toward said lower end, said first sensor being comprised of:
a first antenna body extending from said flange connector to said lower end; and
a first ground electrode extending along said first antenna body from said flange connector to said lower end.

2. The system for measuring multiphase fluid, according to claim 1, wherein said sensor module further comprises:
a first ground ring attached to said first ground electrode; and
a second sensor extending toward said lower end from said first ground ring, said second sensor being comprised of:
a second antenna body extending from said first ground ring to said lower end; and
a second ground electrode extending along said second antenna body toward said lower end,
wherein said first antenna body with said first ground electrode, said first ground ring, and said second antenna body with said second ground electrode span said sample volume so as to simultaneously measure fluids within said set portion of said container according to relative position of said set distance within said container.

3. The system for measuring multiphase fluid, according to claim 2, wherein said first antenna body with said first ground electrode and said second antenna body with said second ground electrode extend through said set portion of said container so as to span said sample volume.

4. The system for measuring multiphase fluid, according to claim 2, wherein said sensor module further comprises:
a second ground ring attached to said second ground electrode; and
a third sensor extending toward said lower end from said second ground ring, said third sensor being comprised of:
a third antenna body extending from said second ground ring to said lower end; and
a third ground electrode extending along said third antenna body toward said lower end,
wherein said first antenna body with said first ground electrode, said first ground ring, said second antenna body with said second ground electrode, said second ground ring, and said third antenna body with said third ground electrode span said sample volume so as to simultaneously measure fluids within said set portion of said container according to relative position of said set distance within said container.

5. The system for measuring multiphase fluid, according to claim 4, wherein said first antenna body with said first ground electrode, said second antenna body with said second ground electrode, and said third antenna body with said third ground electrode extend through said set portion of said container so as to span said sample volume.

6. The system for measuring multiphase fluid, according to claim 1, further comprising:
a pipe connection flange attached to said top end of said container body and removably attached to said flange connector;
a flexible joint connected to said pipe connection flange so as to allow said profiler to swivel relative to said flexible joint; and
a coaxial cable transition box attached to said flexible joint so as to allow electrical connections to said profiler.

7. A profiler to be positioned within a sample supply of multiphase fluid, comprising:
at least one sensor module having a proximal end and a distal end opposite said proximal end, said distal end extending a set distance from said proximal end so as to form a proximal measurement zone and a distal measurement zone;
a flange connector at said proximal end; and
a flange cap at said distal end,
wherein said proximal measurement zone corresponds to a proximal portion of said sample supply of multiphase fluid,
wherein said distal measurement zone corresponds to a distal portion of said sample supply of multiphase fluid, said proximal portion being different from said distal portion,
wherein said proximal measurement zone is separated from said distal measurement zone by said set distance so as to span said at least one sensor module from said proximal portion to said distal portion and simultaneously measure fluids within said proximal measurement zone and said distal measurement zone according to relative position of said proximal portion and said distal portion.

8. The profiler, according to claim 7, wherein said at least one sensor module comprises:
at least one first sensor attached to said flange connector and extending toward said distal end, said first sensor being comprised of:
at least one first antenna body extending from said flange connector to said distal end; and
at least one first ground electrode extending along said first antenna body from said flange connector to said distal end,
wherein said first antenna body with said first ground electrode spans from said proximal portion to said distal portion so as to simultaneously measure fluids within said proximal measurement zone and said distal measurement zone according to relative position of said proximal portion and said distal portion.

9. The profiler, according to claim 7, further comprising:
a container being comprised of a container body with a top end and a bottom end below said top end,
wherein said proximal end is oriented closer to said top end, and
wherein said distal end is oriented closer to said bottom end.

10. The profiler, according to claim 9, further comprising:
a pipe connection flange attached to said top end of said container body and removably attached to said flange connector;
a flexible joint connected to said pipe connection flange so as to allow said profiler to swivel relative to said flexible joint; and
a coaxial cable transition box attached to said flexible joint so as to allow electrical connections to said profiler.

11. A method of measurement, comprising the steps of:
installing a profiler, according to claim 8, in a sample supply of multiphase fluid;
measuring fluid characteristics of said proximal portion of said sample supply of multiphase fluid at said proximal measurement zone with said at least one sensor module;
measuring fluid characteristics of said distal portion of said sample supply of multiphase fluid at said distal measurement zone with said at least one sensor module simultaneous with the step of measuring fluid characteristics of said proximal portion; and
determining a position profile of fluid characteristics of said sample supply of multiphase fluid based on said set distance of said sensor module.

12. The method of measurement, according to claim 11,
wherein said sample supply of multiphase fluid is within a container being comprised of a container body with a top end and a bottom end below said top end,
wherein said proximal end is oriented closer to said top end, and
wherein said distal end is oriented closer to said bottom end,
wherein said container body has a set portion between said top end and said bottom end, said set portion being aligned with said set distance so as to define a sample volume of said container with a relative position within said container, and
wherein said sample volume of said container corresponds to said proximal portion of said sample supply and said distal portion of said sample supply.

13. The method of measurement, according to claim 12,
wherein said position profile of fluid characteristics of said sample supply of multiphase fluid corresponds to said sample volume of said container.

14. The system for measuring, according to claim 2,
wherein said first ground electrode is spirally wound around said first antenna body from said flange connector to said lower end, and
wherein said second ground electrode is spirally wound around said second antenna body from said first ground ring to said lower end.

15. The profiler, according to claim 8, wherein said at least one sensor module further comprises:
a first ground ring attached to said first ground electrode; and
a second sensor extending toward said distal end from said first ground ring, said second sensor being comprised of:
a second antenna body extending from said first ground ring to said distal end; and
a second ground electrode extending along said second antenna body toward said distal end,
wherein said first antenna body with said first ground electrode, said first ground ring, and said second antenna body with said second ground electrode span from said proximal portion to said distal portion so as to simultaneously measure fluids within said proximal measurement zone and said distal measurement zone according to relative position of said proximal portion and said distal portion.

16. The profiler, according to claim 15, wherein said first antenna body with said first ground electrode and said second antenna body with said second ground electrode extend through said proximal measurement zone and said distal measurement zone so as to span said sensor module from said proximal portion to said distal portion.

17. The profiler, according to claim 15, wherein said at least one sensor module further comprises:
a second ground ring attached to said second ground electrode; and
a third sensor extending toward said distal end from said second ground ring, said third sensor being comprised of:
a third antenna body extending from said second ground ring to said distal end; and
a third ground electrode extending along said third antenna body toward said distal end,
wherein said first antenna body with said first ground electrode, said first ground ring, said second antenna body with said second ground electrode, said second ground ring, and said third antenna body with said third ground electrode span from said proximal portion to said distal portion so as to simultaneously measure fluids within said proximal measurement zone and said distal measurement zone according to relative position of said proximal portion and said distal portion.

18. The profiler, according to claim 17, wherein said first antenna body with said first ground electrode, said second antenna body with said second ground electrode, and said third antenna body with said third ground electrode extend through said proximal measurement zone and said distal measurement zone so as to span said sensor module from said proximal portion to said distal portion.

* * * * *